US012564370B2

(12) United States Patent
Joshi

(10) Patent No.: US 12,564,370 B2
(45) Date of Patent: Mar. 3, 2026

(54) METHOD FOR ESTIMATING HEMODYNAMIC PARAMETERS

(71) Applicant: KONINKLIJKE PHILIPS N.V., Eindhoven (NL)

(72) Inventor: Rohan Joshi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 458 days.

(21) Appl. No.: 18/009,586

(22) PCT Filed: Jun. 11, 2021

(86) PCT No.: PCT/EP2021/065761
§ 371 (c)(1),
(2) Date: Dec. 9, 2022

(87) PCT Pub. No.: WO2021/250234
PCT Pub. Date: Dec. 16, 2021

(65) Prior Publication Data
US 2023/0210491 A1 Jul. 6, 2023

(30) Foreign Application Priority Data

Jun. 11, 2020 (EP) ..................................... 20179433
Jun. 10, 2021 (EP) ..................................... 21178746

(51) Int. Cl.
A61B 8/06 (2006.01)
A61B 8/00 (2006.01)
A61B 8/08 (2006.01)
(52) U.S. Cl.
CPC ................ A61B 8/06 (2013.01); A61B 8/085 (2013.01); A61B 8/488 (2013.01)

(58) Field of Classification Search
CPC ........... A61B 8/06; A61B 8/085; A61B 8/488
See application file for complete search history.

(56) References Cited

U.S. PATENT DOCUMENTS

| | | | |
|---|---|---|---|
| 5,515,857 A | * | 5/1996 | Tsujino .................. A61B 8/065 |
| | | | 600/456 |
| 5,997,479 A | | 12/1999 | Savord et al. |
| 6,013,032 A | | 1/2000 | Savord |
| 6,443,896 B1 | | 9/2002 | Detmer |
| 6,530,885 B1 | | 3/2003 | Entrekin et al. |

(Continued)

FOREIGN PATENT DOCUMENTS

| | | | |
|---|---|---|---|
| CN | 109171675 A | 1/2019 | |
| WO | WO-2019234767 A1 * | 12/2019 | ............... A61B 5/02 |

OTHER PUBLICATIONS

Genovese, M., "Ultrasound Transducers," Journal of Diagnostic Medical Sonography. vol. 32, 2016. p. 48-53 (Year: 2016).*

(Continued)

*Primary Examiner* — Sean A Frith

(57) ABSTRACT
A method and system for deriving one or more hemodynamic parameters based on blood-velocity and arterial diameter measures, or parameters proportional thereto, each sampled recurrently or continuously over a time period to obtain for each a data series spanning a time window (i.e. a waveform). This is used, preferably in combination with at least one further physiological parameter, for example heart rate, to derive one or more hemodynamic parameters. A transfer function or machine learning model is used to process the inputs to obtain the estimated hemodynamic parameters.

13 Claims, 7 Drawing Sheets

(56) References Cited

U.S. PATENT DOCUMENTS

| | | | |
|---|---|---|---|
| 6,623,432 B2 | 9/2003 | Powers et al. | |
| 2002/0022785 A1* | 2/2002 | Romano | A61B 5/029 |
| | | | 600/526 |
| 2002/0062086 A1 | 5/2002 | Miele et al. | |
| 2013/0072806 A1* | 3/2013 | Zhang | A61B 5/0205 |
| | | | 600/485 |
| 2013/0310691 A1 | 11/2013 | Furman et al. | |
| 2015/0112901 A1* | 4/2015 | Singer | G06N 5/04 |
| | | | 706/12 |
| 2016/0029995 A1 | 2/2016 | Navratil et al. | |
| 2017/0086780 A1 | 3/2017 | Sokulin et al. | |
| 2018/0125376 A1 | 5/2018 | Denney, Jr. et al. | |
| 2019/0069842 A1* | 3/2019 | Rothberg | A61B 8/4245 |

OTHER PUBLICATIONS

Meinders, J., et al., "Simultaneous Assessment of Diameter and Pressure Waveforms in the Carotid Artery," Ultrasound in Med & Biol,, vol. 30(2). 2004. p. 147-15 (Year: 2004).*

Hoeks, A., et al., "Non-invasive measurement of mechanical properties of arteries in health and disease," Journal of Engineering in Medicine. vol. 213. 1999 p. 1-9 (Year: 1999).*

Huttunen, J., et al. "Pulse transit time estimation of aortic pulse wave velocity and blood pressure using machine learning and simulated training data," Computational Biology. 2019. p. 1-23 (Year: 2019).*

International Search Report and Written Opinion for PCT/EP2021/065761; Mailing date: Sep. 17, 2021, 10 pages.

Balmer, J. et al., "Clinically applicable model-based method, for physiologically accurate flow waveform and stroke volume estimation", Computer Methods and Programs in Biomedicine, 2020, vol. 185, 13 pages.

Bikia, V. et al., "Noninvasive estimation of aortic hemodynamics and cardiac contractility using machine learning", Scientific Reports, 2020, 17 pages.

* cited by examiner

METHOD FOR ESTIMATING HEMODYNAMIC PARAMETERS

This application is the U.S. National Phase application under 35 U.S.C. § 371 of International Application No. PCT/EP2021/065761, filed on Jun. 11, 2021, which claims the benefit of European Applications 20179433.3, filed Jun. 11, 2020, and 21178746.0, filed Jun. 10, 2021. These applications are hereby incorporated by reference herein.

FIELD OF THE INVENTION

This invention relates to a method for non-invasive estimation of hemodynamic parameters.

BACKGROUND OF THE INVENTION

Critically ill patients in an intensive care unit (ICU) and patients in an operating room (OR) require monitoring of various physiological parameters. These include routine vital sign monitoring such as: heart rate (HR), respiratory rate (RR), arterial oxygen saturation (SpO$_2$), temperature and often invasive or non-invasive blood pressure (BP) measurements.

In addition, patients often undergo hemodynamic monitoring. Hemodynamic monitoring attempts to measure forces responsible for circulating blood within the body. It is effectively a performance measure of the cardiovascular system. Typical central hemodynamic parameters include cardiac output (CO), stroke volume (SV) and stroke volume variation.

Hemodynamic monitoring is needed for early detection, identification and management of life-threatening clinical conditions such as sepsis and cardiogenic shock, as well as for assessing the efficacy of pharmaceutical interventions such as the administration of vasopressors.

There are a number of different methods for monitoring hemodynamic parameters. By way of example, there will now be described three clinically prevalent methods for monitoring cardiac output.

A first example is the thermodilution approach. This uses the Swan-Ganz pulmonary artery catheter (PAC). It is widely believed to be the most clinically accurate method for assessing central hemodynamics. It is considered the "gold standard" for hemodynamic monitoring of critically ill cardiac patients and is typically the reference measurement against which new technologies are validated and compared. However, despite this, the Swan-Ganz approach still exhibits significant imprecision, with cardiac output measurements varying up to 10-15%.

A second example method, more recently developed, for cardiac output monitoring is the PiCCO (pulse contour cardiac output) system. This is a less invasive alternative to the PAC, owing to the less critical location of the arterial line placement, which can be in the axillary, brachial, femoral or radial artery. The PiCCO approach also requires a central venous catheter. The PiCCO approach is based on continuous cardiac output monitoring using the method of pulse contour analysis. This involves estimating CO and SV using arterial waveform information, along with intermittent transpulmonary thermodilution, for calibration purposes. In patients who already have a central arterial line, PiCCO requires only the insertion of an arterial catheter, making it less invasive than the Swan Ganz approach. However, the accuracy of the PiCCO measurement is highly dependent on the underlying changes in the systemic vascular resistance (SVR) and on the time interval since the last calibration point (i.e., point in time since last thermodilution). Sudden changes in the SVR, owing to administration of vasoactive drugs render PiCCO measurements inaccurate. Also over time, owing to gradual autonomic regulation, the SVR can undergo changes. For this reason, intermittent calibration of the PiCCO system is needed for obtaining accurate measurements.

As a third example, there exist minimally invasive and non-invasive methods for hemodynamic monitoring. These include the minimally invasive FloTrac® system and the non-invasive ClearSight® system. These each rely on pulse contour analysis, but omit calibration. They are therefore less trusted by clinicians. Such systems perform better for tracking trending of hemodynamic parameters than for obtaining absolute measurements.

The FloTrac® approach employs an invasive peripheral arterial line while the Clearsight® approach uses a finger cuff. Typically, the FloTrac® method has better performance than the ClearSight® method.

Major limitations of the more accurate methods of determining hemodynamic parameters include the high invasiveness of the measuring modality—which also carries increased patient risk—and the high level of skill required to insert arterial lines, especially in the case of the PAC. Furthermore, the PAC and the PiCCO approach both require intermittent calibration to obtain accurate measurements. This is problematic when thermodilution is used for calibration because thermodilution cannot be carried out frequently. Some PAC approaches include a heating element to heat small volumes of blood, thereby allowing continuous thermodilution to calibrate the system.

With regard to FloTrac and ClearSight, these have low accuracy as they are un-calibrated. This also means that they are not reliable for clinically relevant events such as when fluids or medications are administered, due to expected changes in the SVR which occur.

Thus, existing hemodynamic monitoring approaches are either highly invasive, or lack accuracy, or both. It would be of advantage to identify a non-invasive hemodynamic monitoring method with higher accuracy than existing methods.

SUMMARY OF THE INVENTION

The invention is defined by the claims.

According to examples in accordance with an aspect of the invention, there is provided a computer implemented method for deriving one or more hemodynamic parameters of a subject, comprising:

obtaining a blood velocity waveform representative of blood velocity at a measurement location of at least one blood vessel over a time window, preferably wherein the blood velocity waveform is based at least in part on Doppler ultrasound data acquired from the measurement location;

obtaining an arterial diameter waveform representative of a diameter of said at least one blood vessel, or a parameter directly proportional thereto, at the measurement location over the time window, preferably wherein the diameter waveform is based at least in part on ultrasound data from the measurement location;

computing from the blood velocity waveform a pre-defined blood velocity parameter and computing from the arterial diameter waveform a pre-defined arterial diameter parameter;

obtaining data representing at least one pre-defined further parameter for the subject over the time window;

providing the blood velocity parameter, the arterial diameter parameter and the at least one further parameter as a set of inputs to a machine learning model, the machine learning model adapted to process said input parameters and generate an estimate of one or more hemodynamic parameters as an output; and generating a data output indicative of the estimated one or more hemodynamic parameters output by the machine learning model.

Embodiments of the invention are based on utilizing a combination of ultrasound-acquired parameters related to blood flow in an arterial branch of a subject in order to estimate hemodynamic parameters. This is based on research performed by the inventors which found that the blood velocity waveform and arterial diameter waveform, acquired and treated as independent signal sources, are well correlated with central hemodynamics. The method employs use of a statistical or machine learning based model to estimate the central hemodynamics by employing features related to the blood flow parameters measured at an arterial location (e.g. carotid artery). The statistical or machine learning model embodies a pre-determined functional relationship between the inputs and the output hemodynamic parameters. This can be based on a supervised learning or training procedure. It may be based on a regression fitting procedure.

The blood velocity waveform and arterial diameter waveform may for example be obtained either by:

receiving a data input representing the blood velocity waveform and arterial diameter waveform respectively, e.g. from a datastore storing previously derived measurement data, preferably where both waveforms were originally derived from ultrasound data; or receiving Doppler ultrasound data of the at least one blood vessel, and processing the Doppler ultrasound data to derive the blood velocity waveform, and receiving ultrasound imaging data representative of the blood vessel at the measurement location and processing the ultrasound imaging data to derive the arterial diameter waveform.

The ultrasound data may be received from an ultrasound scanning apparatus, or may be received from a datastore, for example storing previously acquired ultrasound data. In either case, the diameter and velocity waveforms should correspond to the same simultaneous time window, e.g. both are derived from the same ultrasound data set for the time window, or the two are derived from simultaneously recorded ultrasound datasets covering the time window.

The hemodynamic parameters are central hemodynamic parameters, e.g. stroke volume, stroke volume variation or cardiac output.

The blood vessel is preferably an artery, for example a peripheral artery. By way of one example, the blood vessel which is used may be the carotid artery.

A blood velocity waveform means a waveform of blood velocity as a function of time over the time window. It may for example be represented in the form of a data series of blood velocity values at intervals over the time window. A diameter waveform means a waveform of blood vessel diameter, or a parameter proportional thereto, as a function of time over the time window. It may for example be represented in the form of a data series of vessel diameter values (or values proportional thereto) at intervals over the time window.

By 'arterial diameter' is meant vessel diameter or a constant multiple or factor thereof, for example arterial radius, or cross-sectional area, or arterial circumference. In general, this parameter may be any dimensional parameter of the blood vessel cross-section, i.e. which is indicative of the size of the width of the lumen of the vessel.

The blood velocity parameter simply means a parameter derived from (processing of) the blood velocity waveform. The arterial diameter parameter simply means a parameter derived from (e.g. processing of) the arterial diameter waveform. For example, each of these parameters may be a statistical parameter of the respective waveform, e.g. a mean value, an area under the waveform (e.g. integral), an interdecile range, a range, a median, a normalization, or any sequential combination of these operations performed on the waveform for example. They might for example otherwise be referred to as a first parameter, derived/extracted from the blood velocity waveform and a second parameter derived/extracted from the arterial diameter waveform.

A machine-learning algorithm is any self-training algorithm that processes input data in order to produce or predict output data. Suitable machine-learning algorithms for being employed in the present invention will be apparent to the skilled person. Examples of suitable machine-learning algorithms include linear regression algorithms, decision tree algorithms and artificial neural networks. Other machine-learning algorithms such as logistic regression, support vector machines or Naïve Bayesian models are suitable alternatives.

In some embodiments, the method may comprise receiving Doppler ultrasound data of the measurement location of said at least one blood vessel, and processing the Doppler ultrasound data to derive the blood velocity waveform.

In some embodiments, the method may comprise receiving ultrasound data of the measurement location of said at least one blood vessel and processing the ultrasound data to derive the arterial diameter waveform.

The ultrasound data may be ultrasound imaging data. It may be B-mode ultrasound data, from which the diameter can be extracted, for example using an automatic segmentation procedure. In further examples, the diameter may be estimated using A-line ultrasound data.

The Doppler ultrasound data may be Pulse Wave Doppler data.

The at least one further parameter is a biological parameter of the subject. It may be a physiological parameter. In some embodiments, the obtaining the at least one further parameter may comprise: receiving ultrasound data of the at least one blood vessel; and processing the ultrasound data to derive the at least one pre-defined further parameter.

For example, the at least one pre-defined further parameter may be derived from the same ultrasound data used to derive one or both of the arterial velocity and arterial diameter waveforms.

Additionally or alternatively, obtaining the at least one further physiological parameter may comprise receiving a sensor signal from one or more physiological parameter sensors, such as a heart/pulse rate sensor, blood oximeter, or blood pressure sensor.

In some embodiments, the computed blood velocity parameter may comprise at least one of: an interdecile range of the velocity waveform over the time window; a mean value of blood velocity over the time window; a mean value of peak systolic velocity over the time window; a mean value of the blood velocity over the time window, normalized by a number of heart cycles spanned by the time window; and/or an integral of the velocity waveform with respect to time over the time window, normalized by the number of heart cycles spanned by the time window.

As will be explained later in this disclosure, these parameters have been found through experimentation to result in particularly good correlation with central hemodynamic parameters.

In some embodiments, the arterial diameter parameter may comprise at least one of: a mean value of the arterial diameter over the time window; and a mean value of a cross-sectional area of the at least one blood vessel over the time window.

In some embodiments, the at least one further physiological parameter may include a heart rate of the subject, and/or a parameter derived therefrom. In some embodiments, the method may comprise receiving Doppler ultrasound data of the at least one blood vessel and processing the Doppler ultrasound data to derive a measure of the heart rate of the subject.

Preferably, the further physiological parameter is derived using the same ultrasound data as is used to derive the blood velocity waveform.

In some embodiments, the at least one further physiological parameter may include a plurality of physiological parameters. In some embodiments, the at least one further physiological parameter may include a set of at least six physiological parameters.

In some embodiments, the obtaining the at least one further physiological parameter may comprise processing the velocity waveform and the arterial diameter waveform to derive an arterial stroke volume waveform. The obtaining the at least one further physiological parameter may further comprise: processing the arterial stroke volume waveform to derive at least one of: an area under the arterial stroke volume waveform over the time window, normalized by a number of heart cycles spanned by the time window; or a mean of the arterial stroke volume waveform over the time window, optionally normalized by a number of heart cycles spanned by the time window.

In particular, deriving the arterial stroke volume waveform may comprise processing the velocity waveform to derive an area under the waveform over a single heart cycle (e.g. through computation of a velocity-time integral of the waveform over a single complete heart cycle), and processing the diameter waveform to derive a cross-sectional area waveform over the same heart cycle. The stroke volume waveform may be derived based on said area under the velocity waveform and based on the cross-sectional area waveform. For example, an average cross-sectional area for the heart cycle may be derived and multiplied by the velocity-time integral result.

In some embodiments, the obtaining the at least one further parameter may comprise: processing the arterial diameter waveform to derive an arterial cross-sectional area waveform for the time window; deriving an arterial blood flow waveform for the time window based on processing of the velocity waveform and the arterial cross-sectional area waveform; and processing the arterial flow waveform to derive a mean arterial flow value over the time window.

Arterial blood flow means blood volume per unit time. The arterial flow waveform may be derived as the product of the arterial cross-sectional area waveform and the arterial velocity waveform.

In some embodiments, the at least one further physiological parameter may comprise one or more vital signs, for example: heart rate, respiration rate, and/or blood pressure. It may additionally or alternatively include one or more demographic parameters such as age, gender, and/or body mass index. These can help improve accuracy in deriving central hemodynamic parameters.

In some embodiments, the one or more hemodynamic parameters may include one or more of: cardiac output, stroke volume, and stroke volume variation.

Preferably, the previously-mentioned time window spans at least one heart-cycle, and more preferably spans a plurality of heart cycles.

In some embodiments, the machine learning algorithm is a multi-parametric linear regression model.

Examples in accordance with a further aspect of the invention a computer program product comprising a computer readable medium, the computer readable medium having computer readable code embodied therein, the computer readable code being configured such that, on execution by a suitable computer or processor, the computer or processor is caused to perform a method in accordance with any example or embodiment outlined above or described below, or in accordance with any claim of this application.

Examples in accordance with a further aspect of the invention provide a processing arrangement comprising: an input/output; and one or more processors. The one or more processors are adapted to perform the following steps:

obtain a blood velocity waveform representative of blood velocity over a time window at a measurement location of at least one blood vessel, preferably wherein the velocity waveform is based at least in part on Doppler ultrasound data of the measurement location;

obtain an arterial diameter waveform representative of a diameter of said at least one blood vessel at the measurement location, or a parameter proportional thereto, over the time window, preferably wherein the arterial diameter waveform is based at least in part on ultrasound imaging data of the measurement location;

compute from the blood velocity waveform a pre-defined blood velocity parameter and compute from the arterial diameter waveform a pre-defined arterial diameter parameter;

obtain data representing value(s) of at least one pre-defined further physiological parameter for the subject over the time window;

provide the blood velocity parameter, the arterial diameter parameter and the at least one further physiological parameter as a set of inputs to a machine learning model, wherein the machine learning model is adapted to receive said set of parameters and to process the parameters to generate an estimate of one or more hemodynamic parameters; and generate a data output indicative of the estimated one or more hemodynamic parameters output by the machine learning model.

Examples in accordance with a further aspect of the invention provide a system. The system comprises a processing arrangement in accordance with any example or embodiment described in this disclosure, or in accordance with any claim of this application. The system further comprises an ultrasound scanning apparatus comprising at least one transducer unit for acquiring ultrasound echo signal data of the at least one blood vessel of the subject, and a processing unit for processing the echo data to derive Doppler ultrasound data and ultrasound image data. The input/output of the processing arrangement is operatively coupled with an output of the ultrasound scanning apparatus for receiving the Doppler ultrasound data and ultrasound image data.

The transducer unit may for example be an ultrasound probe.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

Figure 1:
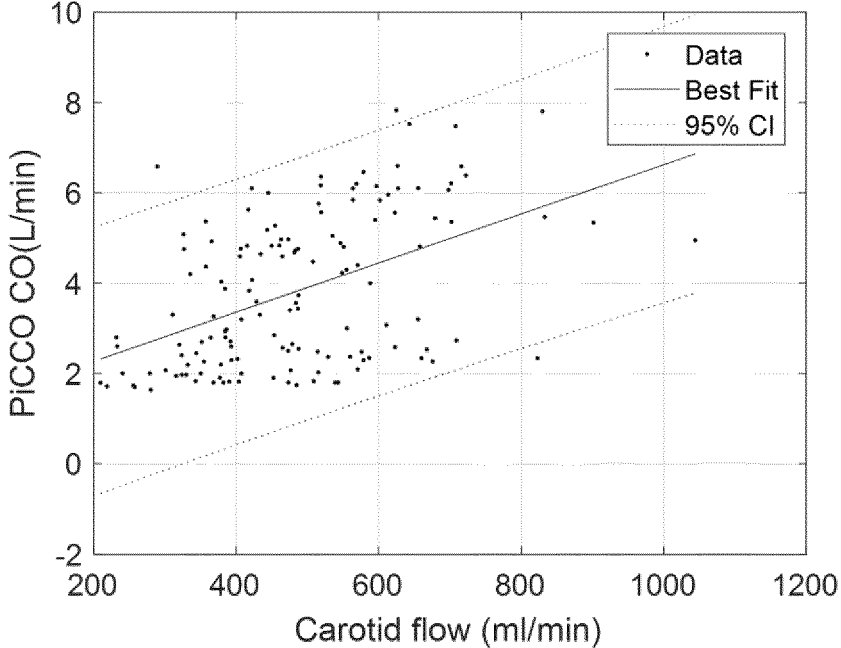
FIG. 1 illustrates an example correlation plot between arterial flow and cardiac output.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for deriving one or more hemodynamic parameters based on blood-velocity and arterial diameter measures, each sampled recurrently or continuously over a time period to obtain for each a data series spanning a time window (i.e. a waveform). This is used, preferably in combination with at least one further physiological parameter, for example heart rate, to derive one or more hemodynamic parameters. A transfer function or machine learning model is used to process the inputs to obtain the estimated hemodynamic parameters.

In order to better understand the invention, there will first be outlined a background explanation of the research study performed by the inventors which informed development of the claimed invention.

The research study was based on the hypothesis that arterial flow measurements related to arterial diameter and blood flow velocity are intrinsically correlated with changes in central hemodynamic parameters such as cardiac output (CO), stroke volume (SV) and stroke volume variation (SVV). An aim was to use ultrasound (US) derived parameters, obtained for example at the carotid artery, to estimate central hemodynamics by developing an appropriate transfer function. Different established hemodynamic modalities, including PiCCO and Flotrac (discussed earlier) served as a reference standard.

A reference clinical dataset was used of previously obtained patient measurements. This included 187 ultrasound measurements at the carotid artery. For each of these, there existed hemodynamic reference measurements of PiCCO (n=140), FloTrac (n=99) and ClearSight (n=73) from 15, 9 and 12 patients respectively.

For each of the ultrasound measurements, US B-mode and US pulse wave Doppler (PWD) data series were available, enabling quasi-continuous measurements of the arterial diameter (from the B-mode data) and the velocity waveform (from the PWD data). Furthermore, the velocity waveform can optionally be used to estimate the heart rate on a beat-to-beat basis. A plurality of parameters were derived from the aforementioned US-based parameters (diameter, velocity waveform and US-based heart rate).

A list of example parameters which may be derived from the arterial diameter and the arterial velocity waveforms are tabulated in Table 1 below.

TABLE 1

| ID | Feature Name | Feature description | Details; Units |
|---|---|---|---|
| 1 | PSV | Peak systolic velocity | Mean of the PSVs in the time window; cm/s |
| 2 | Dia | Diameter | Mean diameter over the time window; cm |
| 3 | VTINormPerBeat | Area under the velocity waveform (velocity-time integral) normalized by the number of heart cycles spanned by the time window | cm/beat |
| 4 | meanVelNormPerBeat | Mean value of the velocity waveform normalized by the number of heart cycles spanned by the time window | cm/s/beat |
| 5 | meanVelWave | Mean value of the velocity waveform | cm/s |
| 6 | IDRVelWave | Interdecile range of the velocity waveform | cm/s |
| 7 | CSArea | Mean Cross-sectional area of the artery | Derived from diameter by assuming circular cross-section; $cm^2$ |
| 8 | ArtSVNormperBeat | Area under the arterial stroke volume (SV) waveform normalized by the number of heart cycles spanned by the time window | ml (SV/beat) |

TABLE 1-continued

| ID | Feature Name | Feature description | Details; Units |
|----|--------------|--------------------|--------------------|
| 9 | meanArtSVWaveNormPerBeat | Mean of the arterial SV waveform normalized by the number of heart cycles spanned by the time window | ml/beat |
| 10 | meanArtSVWave | Mean of the arterial SV waveform. | ml |
| 11 | HR | Mean Heart rate, e.g. derived from the US velocity waveform | bpm |
| 12 | meanArtFlow | Mean of the arterial flow waveform | Velocity waveform multiplied by the Cross-sectional area (waveform); ml/s |
| 13 | ArtFlowVTIArea | Equivalent of arterial flow estimated by multiplying velocity-time integral (VTI) waveform by cross-sectional area divided by length of time window. | ml/s |
| 14 | ArtFlowPSVArea | Equivalent of arterial flow estimated by multiplying PSV by cross-sectional area divided by length of time window. | PSV is not continuous, rather it resets upon each heartbeat; ml/s$^2$ |

Figure 6:
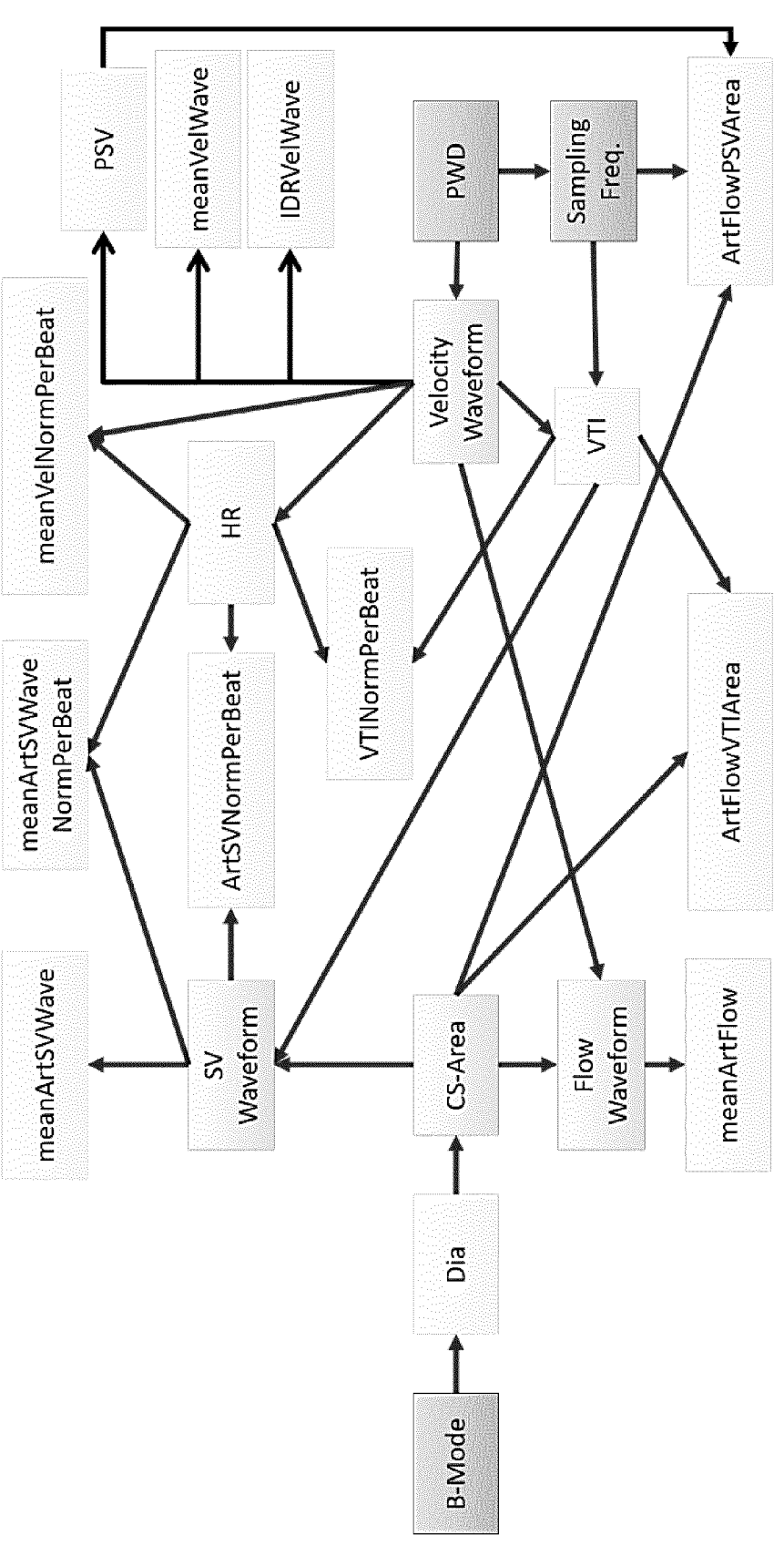
FIG. 6 illustrates dependencies between example input parameters to a machine learning model for deriving estimates of hemodynamic parameters in accordance with one or more embodiments.

The relationships and dependencies between these different parameters are shown in FIG. 6. An arrow leading from a first parameter to a second parameter indicates that the second parameter depends at least in part on the first parameter (i.e. the second parameter may be derived at least in part based on the first). All features are dependent on one or more of the raw US parameters (arterial diameter and velocity waveform).

During the study, the US measurement data for each data entry typically spanned an epoch (time window) of around 30 to 60 s, therefore spanning multiple heart beats. To minimize measurement errors for the derived parameter, all US-based parameters shown in Table 1 were calculated by averaging data from an epoch. For instance, the average (or median) could be of specific landmarks derived from the waveforms such as the average value of all the PSVs within an epoch or the average value of the entire waveform itself, such as the average of the velocity waveform of the epoch. Similarly, the hemodynamic (HDM) reference measurement (PiCCO, FloTrac) is derived based on calculating the mean or median of the HDM reference variable (CO, SV, SVV) in each epoch corresponding to the stored US measurements. Mean and median values of the HDM reference variables were comparable and all analysis in the study was carried out using the median values.

The patient study data were analyzed using a linear multi-parametric transfer function with different ultrasound-derived parameters as inputs and clinical hemodynamic measurements as the reference measurement (the ground truth). The accuracy of the proposed method was assessed on a test dataset by calculating the $R^2$ and RMSE (root mean square error) for CO and SV derived from the transfer function versus CO and SV from the different clinical reference standards. This was performed for different possible combinations of parameters and the success results for each assessed.

As an illustration, the correlation between carotid blood flow (volume per unit time) and PiCCO is relatively poor with an $R^2$ of only 0.22. This result is shown in FIG. 1. This implies that blood flow itself is not a good parameter for estimating central CO. This finding indicates the need for a multiparametric analytical approach to improve the goodness of fit of the transfer function for non-invasively estimating central hemodynamics.

A multiparameteric approach based on linear regression modelling was used to estimate measures of central hemodynamics. A plurality of different combinations of features, derived from blood-flow related parameters, extracted from ultrasound data, were tested by training or fitting respective transfer functions or models to the relevant combination or parameters, and then assessing goodness of fit with the ground truth hemodynamic parameters (as obtained using PiCCO, Flotrac and/or Clearsight methods).

The analytical approach for deriving the transfer function is outlined below.

First, using the reference dataset referred to previously, all available measurements, from all patients combined, were randomly divided into training and test sets of equal size. By way of example, the 140 US-measurements for which PiCCO served as a reference HDM measure were divided into training and tests sets of size 70 each.

Second, for a selection of ultrasound-derived features (e.g. a selection of those outlined in Table 1), the regression model was fitted for one of the HDM reference measurements (e.g. CO, SV) at a time using the data corresponding to the training set. Its performance was then assessed on both the training and test sets. Regression fitting is a well-known technical process and the skilled person will be immediately aware of methods for implementing this, for example least squares, gradient descent, etc. The performance measurements included the goodness-of-fit of linear regression ($R^2$) and the root mean square error (RMSE) obtained from the correlation scatter plot as well as the coefficient of reproducibility (rpc) from the Bland-Altman plot. The coefficient of reproducibility rpc=1.96×SD, where SD is standard deviation.

Third, the second step was repeated 100 times (equivalent to repeated 2-fold cross validation) with a random selection of measurements serving as training and test sets respectively, which were then used to calculate the mean value and standard deviation (estimates of dispersion) of the performance metrics (e.g. $R^2$).

Figure 2:
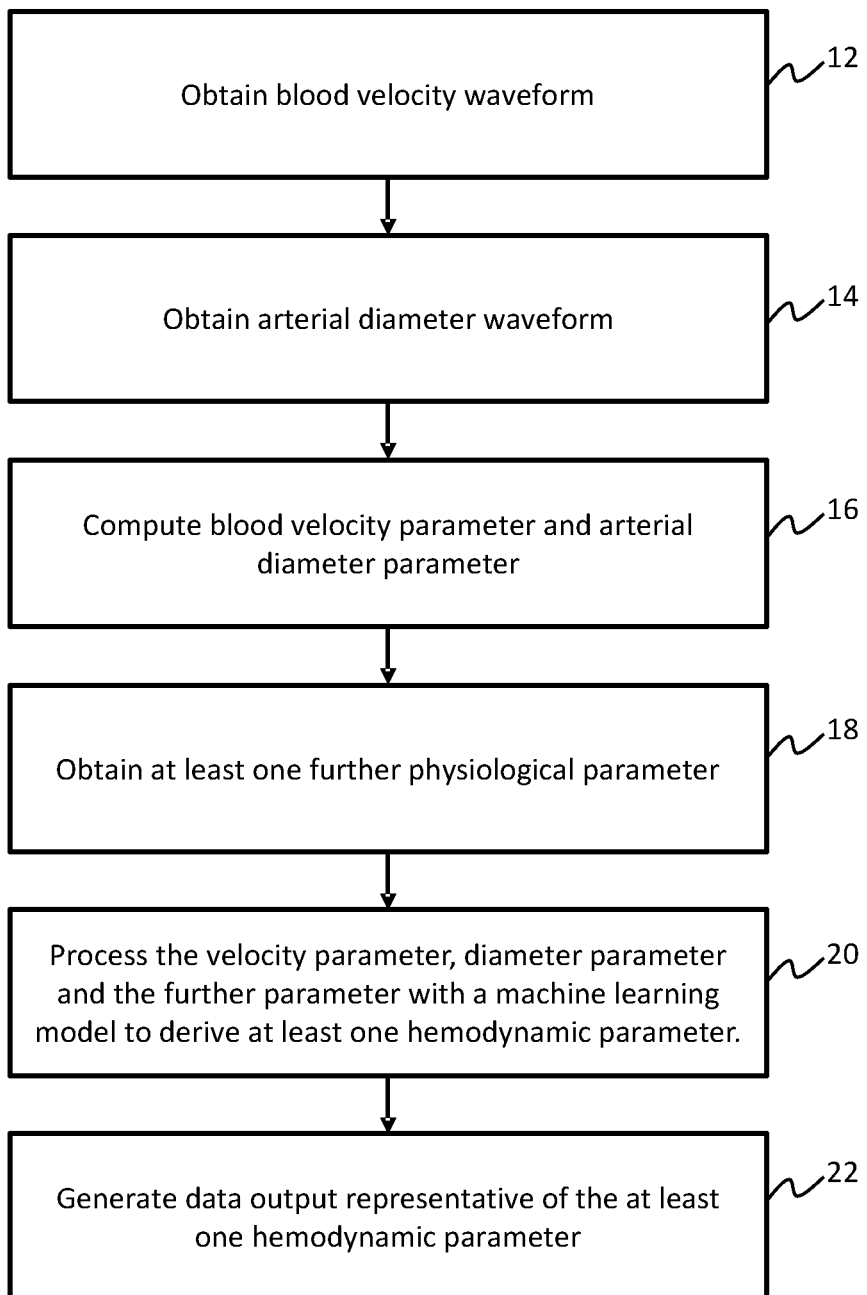
FIG. 2 outlines steps of an example method in accordance with one or more embodiments.

FIG. 2 outlines steps of an example method in accordance with one or more embodiments of the invention. The method may be computer-implemented. The method is for deriving one or more hemodynamic parameters of a subject.

The method comprises obtaining 12 a blood velocity waveform representative of blood velocity at a measurement location of at least one blood vessel over a time window. The blood velocity waveform is based on Doppler ultrasound data acquired from the measurement location.

The blood vessel in some embodiments may be a peripheral artery. A peripheral artery means an artery outside of the heart and brain, e.g. in the neck, arm, leg, hand, or foot.

The blood velocity waveform may be represented by a data series of blood velocity measurement samples, at regular time intervals over a time window (or epoch). The blood velocity waveform can either be received, for example from a datastore or ultrasound scanning apparatus, or may be derived based on received Doppler ultrasound data, e.g. pulse wave Doppler data. The method may be performed in real time with ultrasound data collection, or at a later time based on previously acquired ultrasound measurement data.

The method further comprises obtaining 14 an arterial diameter waveform representative of a diameter of said at least one blood vessel at the measurement location over the time window. The diameter waveform is based on ultrasound data from the measurement location. The ultrasound data may for example be B-mode, C-mode or A-line data. Extracting the diameter measurement may be based on an automated segmentation algorithm or based on another image processing algorithm. The skilled person in this field would be immediately aware of suitable technical means for extracting the diameter measurement from the ultrasound data.

The method further comprises computing 16 from the blood velocity waveform a pre-determined blood velocity parameter and computing from the arterial diameter waveform a pre-determined arterial diameter parameter.

The method further comprises obtaining 18 data representing at least one pre-defined further physiological parameter for the subject over the time window. This further physiological parameter may be a heart rate of the subject, or a parameter derived therefrom. The further physiological parameter may be derived based on one or more of the arterial velocity waveform, arterial diameter waveform and a heart rate measurement.

The method further comprises providing 20 the blood velocity parameter, the arterial diameter parameter and the at least one further physiological parameter as a set of inputs to a statistical or machine learning model, the model trained to process said input parameters and generate an estimate of one or more hemodynamic parameters as an output.

The method further comprises generating 22 a data output indicative of the estimated one or more hemodynamic parameters output by the model. This may be communicated to a user interface in some examples, e.g. a patient monitor system. It may be displayed using a display device. It may be communicated to a data storage unit for later retrieval. It may be communicated to a remote computer or remote datastore via a network or Internet link.

There are different options for the obtaining the data.

In some examples, the method may comprise receiving Doppler ultrasound data of the measurement location of said at least one blood vessel, and processing the Doppler ultrasound data to derive the blood velocity waveform. In other examples, the velocity waveform may be received from an external source.

In some examples, the method may comprise receiving ultrasound data of the measurement location of said at least one blood vessel and processing the ultrasound data to derive the arterial diameter waveform. In other examples, the diameter waveform may be received from an external source.

Regarding the at least one further physiological parameter, the method may comprise receiving the parameter from an external source, e.g. a measurement sensor or patient monitoring system or subsystem. The method may comprise deriving or computing the parameter from received sensing data. It may be derived from ultrasound data in some examples. For instance, in some embodiments, the method may comprise receiving ultrasound data of the at least one blood vessel; and processing the ultrasound data to derive the at least one pre-defined further physiological parameter.

Figure 3:
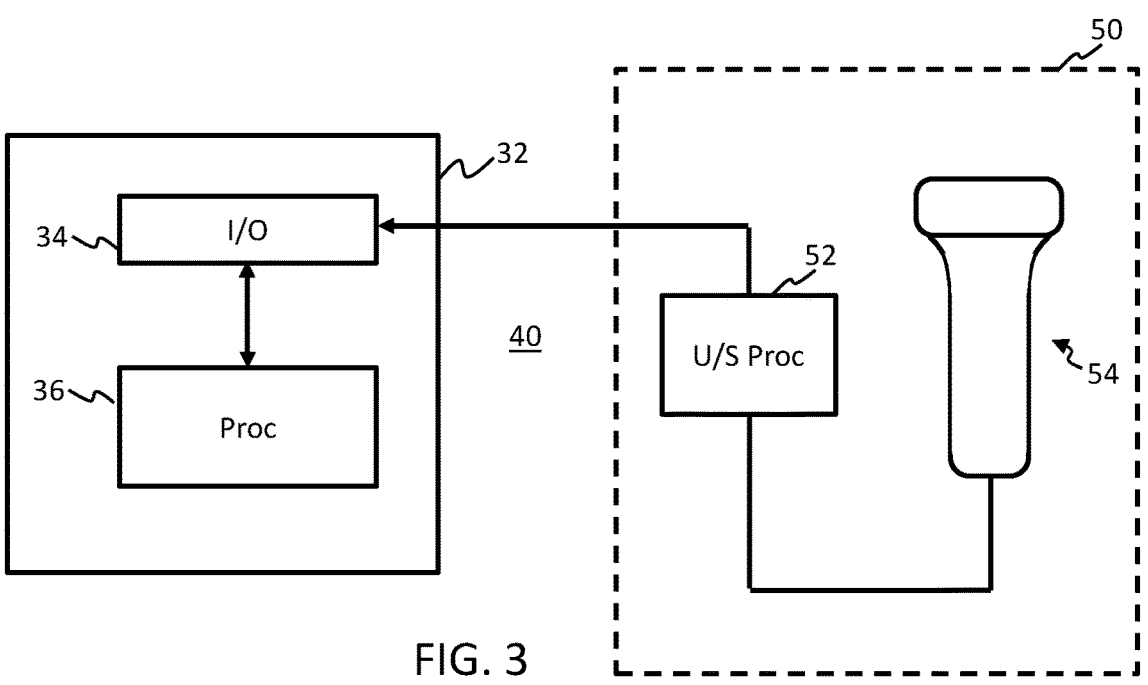
FIG. 3 shows components of an example system in accordance with one or more embodiments.

FIG. 3 shows an example system 40 in accordance with an aspect of the invention. The system includes a processing arrangement 32 comprising an input/output 34; and one or more processors 36. The processing arrangement may in accordance with a further aspect of the invention be provided by itself.

The one or more processors 36 of the processing arrangement are configured to perform the steps of the method outlined above, or in accordance with any embodiment described in this disclosure or any claim of this application.

With regards to the system 40, the system may further comprise an ultrasound scanning apparatus 50 comprising at least one transducer unit 54 for acquiring ultrasound echo signal data of the at least one blood vessel of the subject, and a processing unit 52 for processing the echo data to derive Doppler ultrasound data and ultrasound spatial data (e.g. B-mode data or A-line data).

Figure 4:
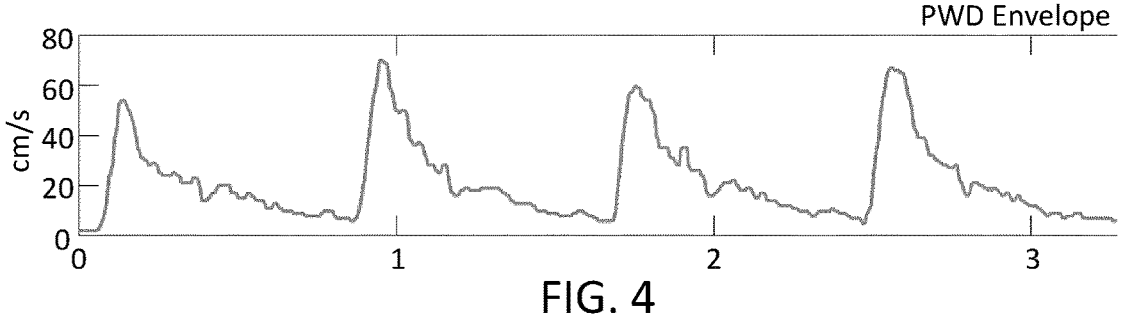
FIG. 4 shows an example pulse wave Doppler signal envelope.

FIG. 4 schematically illustrates an example pulse wave Doppler (PWD) envelope derived from ultrasound echo data. The PWD envelope spans four heart cycles in this example.

Figure 5:
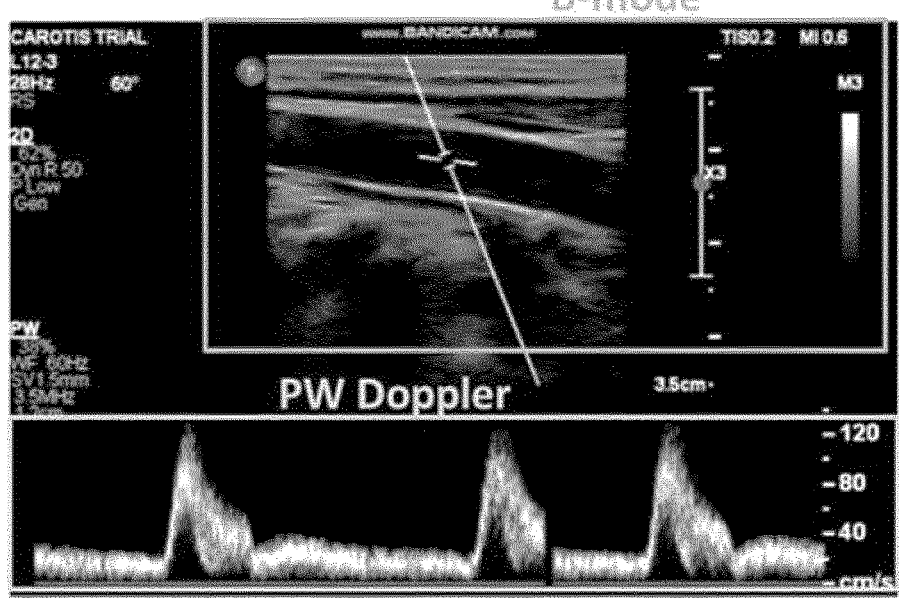
FIG. 5 shows an example display output of an ultrasound scanning apparatus adapted to simultaneously acquire pulse wave Doppler data and B mode data.

FIG. 5 schematically illustrates an example display output of an ultrasound scanning apparatus simultaneously generating B-mode and PWD ultrasound data (Duplex mode). In this example, the ultrasound data represents the carotid artery. A diameter of the artery is automatically extracted by a segmentation algorithm embodied by the ultrasound scanning apparatus.

There are different options in relation to the computed blood velocity parameter, arterial diameter parameter and further physiological parameter, which act as inputs to the machine learning model.

With regards to the blood velocity parameter and diameter parameter, what is meant by these labels is that the parameters are computed or extracted from the blood velocity waveform and arterial diameter waveform. In other words, they are a blood velocity-derived parameter and arterial diameter-derived parameter. They might instead be referred to as first, second and third parameters for example.

Different options for the different parameters will now be discussed, with reference to Table 1 which lists a large number of different parameters.

With regards to the blood velocity parameter, by way of a non-limiting set of examples, this may be any one or more of:

an interdecile range of the velocity waveform over the time window (IDRVelWave in Table 1);

a mean value of blood velocity over the time window (meanVelWave in Table 1);

a mean value of peak systolic velocity over the time window (PSV in Table 1);

a mean value of the blood velocity over the time window, normalized by a number of heart cycles spanned by the time window (meanVelNormPerBeat in Table 1);

an integral of the velocity waveform with respect to time over the time window, normalized by the number of heart cycles spanned by the time window (VTINorm-PerBeat in Table 1).

In some embodiments, a combination or two or more of these parameters may be used as inputs to the transfer function.

With regards to the arterial diameter parameter, this may, according to a non-limiting set of examples, be one or more of:

a mean value of the arterial diameter over the time window (Dia in Table 1);

a mean value of a cross-sectional area of the at least one blood vessel over the time window (CSArea in Table 1).

With regards to the at least one further physiological parameter, this may in some examples include a heart rate of the subject (HR in Table 1). In some embodiments, the method may comprise receiving Doppler ultrasound data of the at least one blood vessel and processing the Doppler ultrasound data to derive a measure of the heart rate of the subject.

In some examples, the at least one further parameter may include a parameter derived from processing of a stroke volume waveform. For example, the method may comprise processing the velocity waveform and the arterial diameter waveform to derive an arterial stroke volume waveform. The arterial stroke volume waveform can be computed by processing the velocity waveform to derive an area under the waveform over a single heart cycle (e.g. through computation of a velocity-time integral of the waveform over a single complete heart cycle), and processing the diameter waveform to derive a cross-sectional area waveform over the same heart cycle. The stroke volume waveform may be derived based on said area under the velocity waveform and based on the cross-sectional area waveform.

By way of one example, the at least one further parameter may include an area under the arterial stroke volume waveform over the time window, normalized by a number of heart cycles spanned by the time window.

Additionally or alternatively, the at least one further parameter may include a mean of the arterial stroke volume waveform over the time window, optionally normalized by a number of heart cycles spanned by the time window.

In some examples, the at least one further parameter may include a mean arterial blood flow value for the time window (volume flow per unit time). This may be computed by processing the arterial diameter waveform to derive an arterial cross-sectional area waveform for the time window; deriving an arterial blood flow waveform for the time window based on computing a product of the velocity waveform and the arterial cross-sectional area waveform; and processing the arterial flow waveform to derive a mean arterial flow value over the time window.

In some examples, the at least one further physiological parameter may include one or more vital signs, for example: heart rate, respiration rate, and/or blood pressure. In some examples, these may be obtained from sensor signals received from one or more physiological parameter sensors.

In some embodiments, the machine learning model may be adapted to receive as a further input one or more demographic features of the subject, for example age, gender and/or body mass index (BMI).

Table 1 provides a summary of one non-limiting set of example parameters, some or all of which may be selected as the inputs to be obtained and provided to the machine learning model in order to derive the one or more hemodynamic parameters.

With regards to the derived one or more hemodynamic parameters, these may include, by way of non-limiting example, one or more of: cardiac output, stroke volume, and stroke volume variation.

As described above, the processing of the parameters to derive the one or more hemodynamic parameters is performed using a machine learning model comprising one or more machine learning algorithms which have been trained to map a pre-defined set of input parameters to a set of one or more hemodynamic parameters.

A machine-learning algorithm is any self-training algorithm that processes input data in order to produce or predict output data. Here, the input data comprises the pre-selected blood velocity parameter, arterial diameter parameter, and the further parameter, and the output data comprises the one or more hemodynamic parameters.

Suitable machine-learning algorithms for being employed in the present invention will be apparent to the skilled person. Examples of suitable machine-learning algorithms include linear regression algorithms, decision tree algorithms and artificial neural networks. Other machine-learning algorithms such as logistic regression, support vector machines or Naïve Bayesian models are suitable alternatives.

In examples presented below, a machine learning algorithm in the form of a multi-parametric linear regression model is used to demonstrate the principles of the inventive concept. However, it is to be understood that, in each example, the machine learning model may be replaced by a different type of machine learning model without impact on the advantages technical effects.

With regards in particular to a multi-parametric linear regression model, the model is established by first constructing a model or algorithm which incorporates each of the desired input parameters as an (independent variable) parameter of the model, with a corresponding coefficient or weighting, and secondly training the constructed model based on a training dataset to thereby fit the model coefficients or weightings so as to provide a best fit between the input parameters of the training dataset and the corresponding output parameters of the training dataset. The desired input parameters form the independent variables of the model, while the target hemodynamic parameter is the dependent variable of the model. The model represents the relevant hemodynamic parameter being estimated as being a linear sum of a constant term (the intercept), and each of the dependent variables multiplied by a respective weighting or coefficient.

The training dataset will comprise training input data entries and corresponding training output data entries. The training input data entries in this case correspond to example values of the pre-selected blood velocity parameter, arterial diameter parameter, and further physiological parameter. The training output data entries correspond to pre-determined one or more hemodynamic parameters.

An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For a multiparametric regression model, the training process is a process of fitting the model weightings/coefficients to the training dataset. Once the training or fitting process is complete, the model can be deployed using the weightings or coefficients obtained in the training or fitting process to map input parameters (independent variables) to the output hemodynamic parameter.

The performance or accuracy of a generated machine learning model can be assessed by running the model on a test dataset after training, and assessing the error between the output predicted values generated by the model and the In this example, the PiCCO and FloTrac methods served as reference measurements (ground truth) for both the training data set and test data set. The performance metrics (e.g. $R^2$) are calculated as the mean and standard deviation (SD) of 100 runs of the training and test sets that were randomly selected from the available pool of data.

TABLE 2

| HDM Reference | PiCCO CO | FloTrac CO | PiCCO SV | FloTrac SV |
|---|---|---|---|---|
| n = Training | 70 | 50 | 70 | 50 |
| n = Testing | 70 | 49 | 70 | 49 |
| Transfer function input parameters | IDRVelWave + Dia + HR | IDRVelWave + Dia + HR | IDRVelWave + Dia + HR | IDRVelWave + Dia + HR |
| No of input parameters of transfer function | 3 | 3 | 3 | 3 |
| $R^2$ Training | 0.42 (0.08) | 0.58 (0.09) | 0.28 (0.04) | 0.33 (0.09) |
| RMSE Training | 0.82 (0.07) L/min | 0.72 (0.08) L/min | 9.69 (0.72) ml/beat | 8.51 (1.15) ml/beat |
| rpc (1.96 SD) Training | 2.55 (0.14) L/min | 1.85 (0.12) L/min | 35.33 (2.0) ml/beat | 28.83 (2.57) ml/beat |
| $R^2$ Test | 0.39 (0.09) | 0.55 (0.09) | 0.25 (0.04) | 0.29 (0.13) |
| RMSE Test | 0.87 (0.14) L/min | 0.78 (0.19) L/min | 10.34 (1.52) ml/beat | 9.82 (3.63) ml/beat |
| rpc (1.96 SD) Test | 2.52 (0.17) L/min | 2.07 (0.11) L/min | 37.49 (2.23) ml/beat | 32.29 (4.27) ml/beat | actual ground truth values. For example, for a linear regression model, the performance measurements can include a goodness-of-fit of linear regression ($R^2$), the root mean square error (RMSE) obtained from a correlation scatter plot as well as the coefficient of reproducibility (rpc) obtained from a Bland-Altman plot.

A number of particular examples will now be described, which represent preferred embodiments of the invention.

According to one or more embodiments, the parameters used as inputs to derive the hemodynamic parameter include the following:

any of the blood-velocity related parameters listed in Table 1 above such as PSV, VTINormPerBeat, meanVelNormPerBeat, meanVelWave, and/or IDRVelWave, preferably derived from pulse wave Doppler (PWD) data;

the mean diameter over the time window (Dia in Table 1), e.g. derived from B-mode ultrasound data; and the mean heart rate over the time window (HR in Table 1), for example derived from pulse wave Doppler (PWD) data.

In a preferred example, the blood velocity parameter used is IDRVelWave (interdecile range of the velocity waveform over the time window). These three features originate from different sources and provide complimentary information for estimating the CO and the SV.

In tests, a set of different multi-parametric linear regression models were generated, each configured to map this set of inputs to one of cardiac output (CO) and stroke volume (SV), and these models were trained using a training dataset. Table 2 below shows a summary of performance statistics of the models on a test dataset, based on comparison with hemodynamic reference values ("HDM Reference").

For each model, Table 2 lists the input parameters which the model is adapted to accept, i.e. the independent parameters of the model. In each case, the output value of the model, i.e. the dependent variable, is the particular hemodynamic parameter listed in the HDM Reference entry, i.e. CO or SV.

The $R^2$ for the test set may be used as the primary performance metric followed by RMSE and the rpc. In particular, the difference between the performance metrics of the training and test sets as well as the SD of the estimated metrics give an indication of model overfitting. For instance, the decrease in $R^2$ from training to test sets is relatively small indicating that there is not much evidence of overfitting. In other words, the model is relatively robust and will work well for a comparable patient population.

Figure 7:
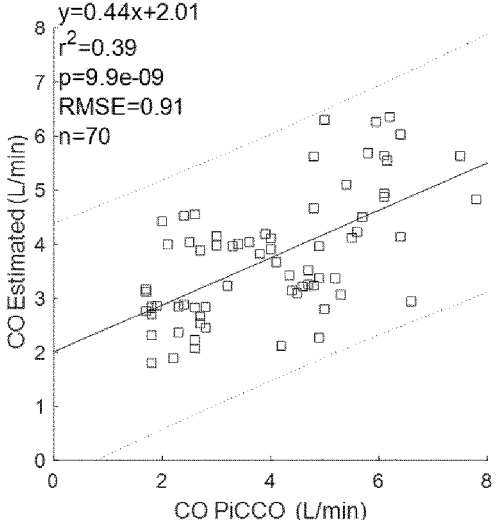
FIGS. 7-9 show accuracy results for a set of three different machine learning models suitable for use in accordance with one or more embodiments.
Figure 7:
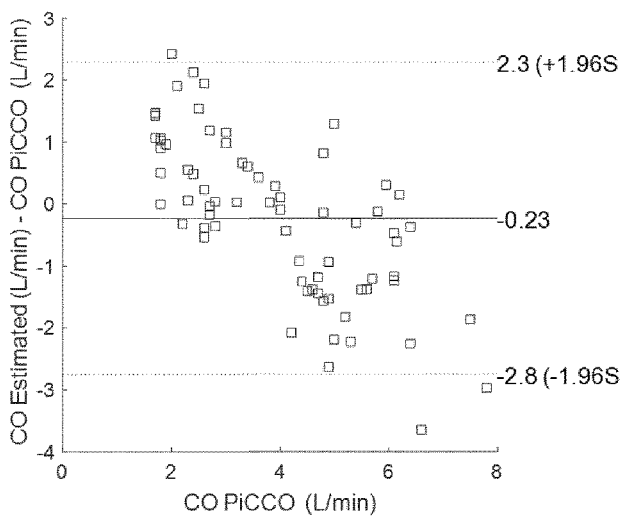

FIG. 7 (left) shows the correlation plot and FIG. 7 (right) shows the Bland-Altman plot for the performance of the transfer function outlined in column 2 of Table 2 when applied to the data set, while PiCCO measurements served as the reference standard.

According to a second embodiment, a greater number of input parameters can be used, for example incorporating several blood-velocity derived parameters, arterial diameter parameters and/or HR-related parameters. These are, physiologically speaking, preferred features. In comparison to the embodiment described above, a greater number of features are incorporated to improve the performance of the model or transfer function. Performance is improved since the combined parameters provide complementary information. Furthermore, several of the combined parameters are more robust measures (e.g. IDRVelWave compared to PSV) of the underlying signal (blood velocity) and are robust to artifacts in the signal.

Table 3 below shows a summary of a set of models built in accordance with this embodiment, and performance statistics thereof when applied to a test dataset, based on comparison with hemodynamic reference values ("HDM Reference"). Each model was built to map the set of input parameters to one of CO or SV.

In this example, the PiCCO and FloTrac methods served as reference measurements (ground truth) for both the training data set and test data set. The performance metrics (e.g. $R^2$) are calculated as the mean and standard deviation (SD) of 100 runs of the training and test sets that were randomly selected from the available pool of data.

As noted above, methods according to embodiments of the present invention may find advantageous application for

TABLE 3

| HDM Reference | PiCCO CO | FloTrac CO |
|---|---|---|
| n = Training | 70 | 50 |
| n = Testing | 70 | 49 |
| Transfer function input parameters | PSV + Dia + VTINormPerBeat + meanVelWave + IDRVelWave + meanArtSVWaveNormPerBeat + meanArtSVWave + ArtFlowPSVArea | PSV + Dia + IDRVelWave + meanArtSVWaveNormPerBeat + HR + meanArtFlow |
| No of input parameters of transfer function | 8 | 6 |
| $R^2$ Training | 0.70 (0.06) | 0.64 (0.06) |
| RMSE Training | 0.76 (0.04) L/min | 0.73 (0.07) L/min |
| rpc (1.96 SD) Training | 1.77 (0.17) L/min | 1.77 (0.20) L/min |
| $R^2$ Test | 0.63 (0.06) | 0.56 (0.07) |
| RMSE Test | 0.90 (0.14) L/min | 0.81 (0.13) L/min |
| rpc (1.96 SD) Test | 2.04 (0.20) L/min | 1.98 (0.21) L/min |

| HDM Reference | PiCCO SV | FloTrac SV |
|---|---|---|
| n = Training | 70 | 50 |
| n = Testing | 70 | 49 |
| Transfer function input parameters | PSV + Dia + meanVelWave + meanArtSVWaveNormPerBeat + meanArtSVWave + ArtFlowPSVArea + HR | PSV + Dia + IDRVelWave + meanArtSVWaveNormPerBeat + HR + meanArtFlow |
| No of input parameters of transfer function | 7 | 6 |
| $R^2$ Training | 0.64 (0.07) | 0.56 (0.07) |
| RMSE Training | 10.27 (0.71) ml/beat | 9.09 (0.62) ml/beat |
| rpc (1.96 SD) Training | 25.06 (2.92) ml/beat | 23.67 (2.1) ml/beat |
| $R^2$ Test | 0.55 (0.07) | 0.42 (0.10) |
| RMSE Test | 11.71 (1.76) ml/beat | 10.91 (2.3) ml/beat |
| rpc (1.96 SD) Test | 28.75 (2.82) ml/beat | 28.26 (3.26) ml/beat |

The input parameter labels used in row 4 correspond to those recited in Table 1 above.

Figure 8:
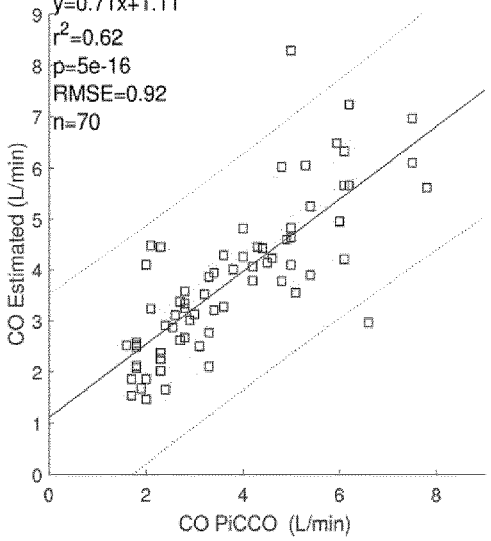
Figure 8:
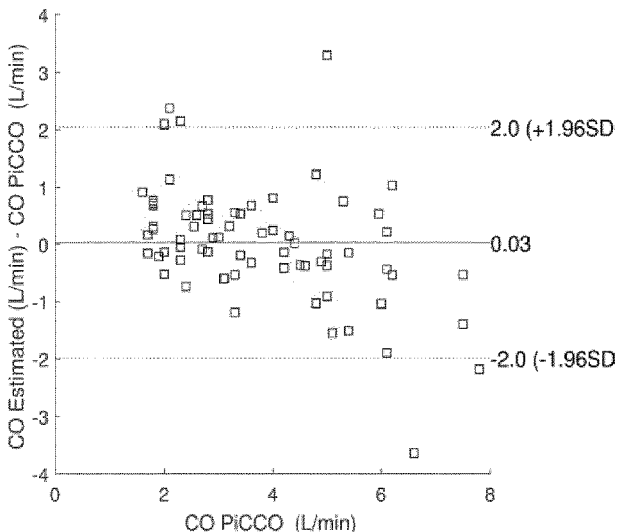
Figure 9:
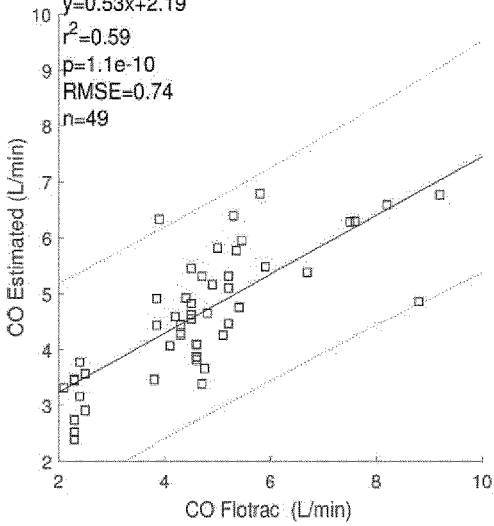
Figure 9:
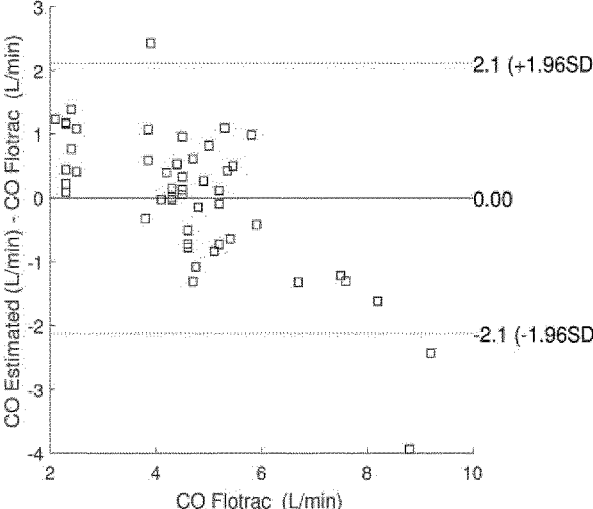

By way of illustration, FIG. 8 shows the performance of the model outlined in column 1 of Table 3, which was configured to generate an estimate of cardiac output (CO), with a PiCCO method measure as a ground truth reference. FIG. 8 (left) shows a correlation plot and FIG. 8 (right) shows the Bland-Altman plot for the performance of the transfer function. FIG. 9 shows the performance of the model outlined in column 2 of Table 3, which was configured to generate an estimate of cardiac output (CO), with a FloTrac method measure as a ground truth reference. FIG. 9 (left) shows a correlation plot and FIG. 9 (right) shows the Bland-Altman plot for the performance of the transfer function.

Comparing the results for the models of Table 2 with those of Table 3, it can be seen that for instance the PiCCO-reference CO transfer function has improved in performance by incorporating 8 features as opposed to 3 (the $R^2$ increases). This is quantitative evidence that multiple features (e.g., PSV, meanVelWave and IDRVelWave) mined from the PWD velocity waveform can provide complimentary information that improves performance of the machine learning model. Moreover, the performance of the model is comparable or even superior to clinical standards such as FloTrac and ClearSight.

continuous or ongoing monitoring of hemodynamics of a subject. The method may comprise generating a data output indicative of the estimated one or more hemodynamic parameters generated by the model and transmitting the data output to a patient monitor system, and wherein the patient monitor system comprises a display device and is adapted to display a visual representation of the derived one or more hemodynamic parameters on the display device. The patient monitor system may additionally or alternatively store or cache the derived hemodynamic parameters, either locally or remotely. It may export the parameters to a remote system, e.g. an institution network or server.

In accordance with a further aspect of the invention, there is provided a method of providing a machine learning model for deriving one or more hemodynamic parameters. The method comprises generating an initial machine learning model adapted to receive a pre-defined set of parameters as inputs, and to process said received parameters to generate an estimate of one or more hemodynamic parameters. The pre-defined set of input parameters include: a parameter computed from a blood velocity waveform representative of blood velocity at a measurement location of at least one blood vessel over a time window; a parameter extracted from an arterial diameter waveform representative of a diameter of said at least one blood vessel at the measurement location over the time window; and at least one pre-defined further physiological parameter for the subject over the time window.

The method further comprises providing a training dataset comprising a plurality of training input data entries and a corresponding plurality of training output data entries, the training input data entries each comprising values for each of the set of pre-defined input parameters, and the training output data entries each comprising corresponding values for the one or more hemodynamic parameters.

The method further comprises applying the machine learning algorithm to the training input data entries and adjusting internal parameters of the machine learning model to minimize error between the generated outputs of the model and the training output data entries.

As noted above, certain embodiments may include an ultrasound scanning apparatus, or means for processing ultrasound echo data to derive further data.

Figure 10:
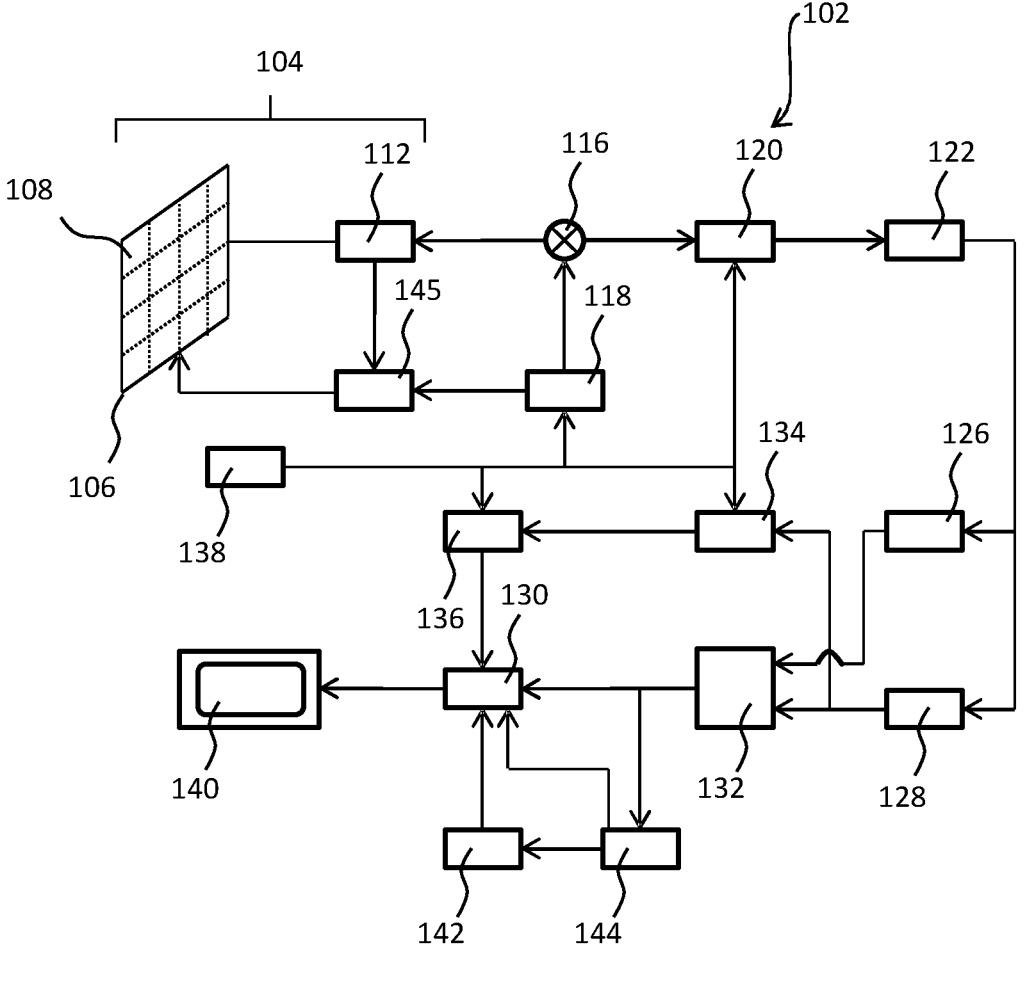
FIG. 10 shows an example ultrasound system.

By way of further, more detailed explanation, the general operation of an exemplary ultrasound system will now be described, with reference to FIG. 10.

The system comprises an array transducer probe 104 which has a transducer array 106 for transmitting ultrasound waves and receiving echo information. The transducer array 106 may comprise CMUT transducers; piezoelectric transducers, formed of materials such as PZT or PVDF; or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is in general entirely optional. Further, the system includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of the user interface or control panel 138. The controller 118 can include transmission circuitry arranged to drive the transducer elements of the array 106 (either directly or via a microbeamformer) during the transmission mode.

The function of the control panel 138 in this example system may be facilitated by an ultrasound controller unit according to an embodiment of the invention.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 10 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 128 processes temporally distinct signals arising from tissue movement and blood flow for the detection of moving substances, such as the flow of blood cells in the image field. The Doppler processor 128 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for optional display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made.

Output data from the quantification processor is coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name. The user interface is also coupled to the transmit controller 118 to control the generation of ultrasound signals from the transducer array 106 and hence the images produced by the transducer array and the ultrasound system. The transmit control function of the controller 118 is only one of the functions performed. The controller 118 also takes account of the mode of operation (given by the user) and the corresponding required transmitter configuration and bandpass configuration in the receiver analog to digital converter. The controller 118 can be a state machine with fixed states.

The user interface is also coupled to the multi-planar reformatter 144 for selection and control of the planes of multiple multi-planar reformatted (MPR) images which may be used to perform quantified measures in the image field of the MPR images.

The above described ultrasound system may be operatively coupled with the processing arrangement 32 previously described. The processing arrangement may receive Doppler ultrasound data and spatial ultrasound data (e.g. B-mode) from the above-described ultrasound system. For example, the above-described ultrasound system may be used to implement the ultrasound sensing apparatus 50 of the system 40 shown in FIG. 3 in some examples.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to".

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

What is claimed is:

1. A method for deriving one or more central hemodynamic parameters of a subject, comprising:

receiving Doppler ultrasound data at a measurement location of at least one peripheral blood vessel from an ultrasound scanning apparatus comprising an ultrasound transducer;

receiving ultrasound data at the measurement location of said at least one peripheral blood vessel from the ultrasound scanning apparatus comprising the ultrasound transducer;

obtaining a blood velocity waveform representative of blood velocity at the measurement location of the at least one peripheral blood vessel over a time window, wherein the blood velocity waveform is based at least in part on Doppler ultrasound data acquired from the measurement location;

obtaining an arterial diameter waveform representative of a diameter of said at least one peripheral blood vessel, or a parameter proportional thereto, at the measurement location over the time window, wherein the diameter waveform is based at least in part on ultrasound data from the measurement location;

computing from the blood velocity waveform a pre-defined blood velocity parameter and computing from the arterial diameter waveform a pre-defined arterial diameter parameter;

obtaining data representing at least one pre-defined further physiological parameter for the subject over the time window;

providing the blood velocity parameter, the arterial diameter parameter and the at least one further physiological parameter as a set of inputs to a trained machine learning model, the machine learning model adapted to process said input parameters and generate an estimate of one or more central hemodynamic parameters as an output; and generating a data output indicative of the estimated one or more central hemodynamic parameters output by the machine learning model, wherein the machine learning model is trained, prior to the providing step, on a training dataset that pairs previously obtained input parameters related to the blood velocity, the arterial diameter, and the further physiological parameter with a reference standard central hemodynamic parameter.

2. The method of claim 1, wherein obtaining the at least one further physiological parameter comprises:

receiving from the ultrasound scanning apparatus comprising the ultrasound transducer ultrasound data of the at least one peripheral blood vessel; and processing the ultrasound data to derive the at least one pre-defined further physiological parameter.

3. The method of claim 1, wherein the blood velocity parameter comprises at least one of:

an interdecile range of the velocity waveform over the time window;

a mean value of blood velocity over the time window;

a mean value of peak systolic velocity over the time window;

a mean value of the blood velocity over the time window, normalized by a number of heart cycles spanned by the time window; or an integral of the velocity waveform with respect to time over the time window, normalized by the number of heart cycles spanned by the time window.

4. The method of claim 1, wherein the arterial diameter parameter comprises at least one of:

a mean value of the arterial diameter over the time window; or a mean value of a cross-sectional area of the at least one peripheral blood vessel over the time window.

5. The method of claim 1, wherein the at least one further physiological parameter includes a heart rate of the subject, and/or a parameter derived therefrom; and wherein the method further comprises receiving Doppler ultrasound data of the at least one peripheral blood vessel and processing the Doppler ultrasound data to derive a measure of the heart rate of the subject.

6. The method of claim 1, wherein the obtaining the at least one further physiological parameter comprises:

processing the velocity waveform and the arterial diameter waveform to derive an arterial stroke volume waveform; and processing the arterial stroke volume waveform to derive at least one of:

an area under the arterial stroke volume waveform over the time window, normalized by a number of heart cycles spanned by the time window; and a mean of the arterial stroke volume waveform over the time window.

7. The method of claim 1, wherein the obtaining the at least one further parameter comprises:

processing the arterial diameter waveform to derive an arterial cross-sectional area waveform for the time window;

deriving an arterial blood flow waveform for the time window based on processing of the velocity waveform and the arterial cross-sectional area waveform; and processing the arterial flow waveform to derive a mean arterial flow value over the time window.

8. The method of claim 1, wherein the at least one further physiological parameter comprises one or more of heart rate, respiration rate, and blood pressure.

9. The method of claim 1, wherein the one or more hemodynamic parameters include one or more of: cardiac output, stroke volume, and stroke volume variation.

10. The method of claim 1, wherein the time window spans at least one heart-cycle.

11. The method of claim 1, wherein the machine learning model is a multi-parametric linear regression model.

12. A non-transitory computer readable medium having computer readable code embodied therein, the computer readable code being configured such that, on execution by a suitable computer or processor, the computer or processor is caused to perform the method as claimed in claim 1.

13. A system for estimating a central hemodynamic parameter from ultrasound Doppler data and imaging data comprising:

a processing arrangement comprising:

an input/output; and one or more processors, adapted to:

obtain a blood velocity waveform representative of blood velocity over a time window at a measurement location of at least one peripheral blood vessel, wherein the velocity waveform is based at least in part on Doppler ultrasound data of the measurement location;

obtain an arterial diameter waveform representative of a diameter of said at least one peripheral blood vessel, or a parameter proportional thereto, at the measurement location over the time window, wherein the arterial diameter waveform is based at least in part on ultrasound imaging data of the measurement location;

compute from the blood velocity waveform a pre-defined blood velocity parameter and compute from the arterial diameter waveform a pre-defined arterial diameter parameter;

obtain data representing at least one pre-defined further physiological parameter for the subject over the time window;

provide the blood velocity parameter, the arterial diameter parameter and the at least one further physiological parameter as a set of inputs to a machine learning model, wherein the machine learning model is adapted to receive said set of parameters and to process the parameters to generate an estimate of one or more central hemodynamic parameters; and generate a data output indicative of the estimated one or more central hemodynamic parameters output by the machine learning model, wherein the machine learning model is trained, prior to the providing step, on training dataset that pairs previously obtained input parameters related to the blood velocity, the arterial diameter, and the further physiological parameter with a reference standard central hemodynamic parameter; and an ultrasound scanning apparatus comprising at least one transducer unit for acquiring ultrasound echo signal data of the at least one peripheral blood vessel of the subject, and a processing unit for processing the echo data to derive Doppler ultrasound data and ultrasound image data;

wherein the input/output of the processing arrangement is operatively coupled with an output of the ultrasound scanning apparatus for receiving the Doppler ultrasound data and ultrasound image data.

\* \* \* \* \*